United States Patent [19]
Martinez et al.

[11] Patent Number: 5,849,031
[45] Date of Patent: Dec. 15, 1998

[54] METHOD AND APPARATUS FOR TERMINATION OF TACHYARRHYTHMIAS

[75] Inventors: Gonzalo Martinez, Mendota Heights; David Lipson; Timothy G. Laske, both of Shoreview, all of Minn.

[73] Assignee: Medtronic, Inc., Minneapolis, Minn.

[21] Appl. No.: 991,838

[22] Filed: Dec. 16, 1997

[51] Int. Cl.⁶ .............................. A61N 1/05; A61N 1/39
[52] U.S. Cl. ................................... 607/121; 607/5
[58] Field of Search ................... 607/119, 120, 607/121, 122, 123, 5

[56] References Cited

U.S. PATENT DOCUMENTS

| | | |
|---|---|---|
| 4,440,178 | 4/1984 | Bussard et al. . |
| 4,602,637 | 7/1986 | Elmqvist et al. . |
| 4,603,704 | 8/1986 | Mund et al. . |
| 4,608,986 | 9/1986 | Beranek et al. . |
| 4,679,572 | 7/1987 | Baker, Jr. . |
| 4,817,634 | 4/1989 | Holleman et al. . |
| 4,821,723 | 4/1989 | Baker, Jr. et al. . |
| 4,850,357 | 7/1989 | Bach, Jr. . |
| 4,860,446 | 8/1989 | Lessar et al. . |
| 4,922,927 | 5/1990 | Fine et al. . |
| 4,953,551 | 9/1990 | Mehra et al. . |
| 4,969,463 | 11/1990 | Dahl et al. . |
| 5,014,696 | 5/1991 | Mehra . |
| 5,016,645 | 5/1991 | Williams et al. . |
| 5,107,834 | 4/1992 | Ideker et al. . |
| 5,193,540 | 3/1993 | Schulman et al. . |
| 5,224,491 | 7/1993 | Mehra . |
| 5,261,400 | 11/1993 | Bardy . |
| 5,265,623 | 11/1993 | Kroll et al. . |
| 5,306,291 | 4/1994 | Kroll et al. . |
| 5,312,439 | 5/1994 | Loeb . |
| 5,324,309 | 6/1994 | Kallok . |
| 5,326,448 | 7/1994 | Otten . |
| 5,336,254 | 8/1994 | Brennen et al. . |
| 5,342,414 | 8/1994 | Mehra . |
| 5,496,362 | 3/1996 | KenKnight et al. . |
| 5,683,443 | 11/1997 | Munshi et al. ............... 607/121 |

*Primary Examiner*—Scott M. Getzow
*Attorney, Agent, or Firm*—Reed A. Duthler; Harold R. Patton

[57] ABSTRACT

An implantable medical lead for use with an implantable cardioverter defibrillator, a method of manufacture and a system employing the lead and cardioverter/defibrillator in combination. The lead is provided with an elongated insulative lead body carrying a cardioversion/defibrillation electrode, which includes a first portion displaying essentially equal attenuation of positive and negative voltage pulses and a second portion displaying differential attenuation of positive and negative voltage pulses. The cardioveter/defibrillator provides a biphasic pulse in which a higher amplitude phase of the pulse is differentially attenuated by the electrode. The electrode is fabricated in whole or in part of a valve metal such as tantalum, anodized and annealed to provide a thick, durable oxide coating.

36 Claims, 10 Drawing Sheets

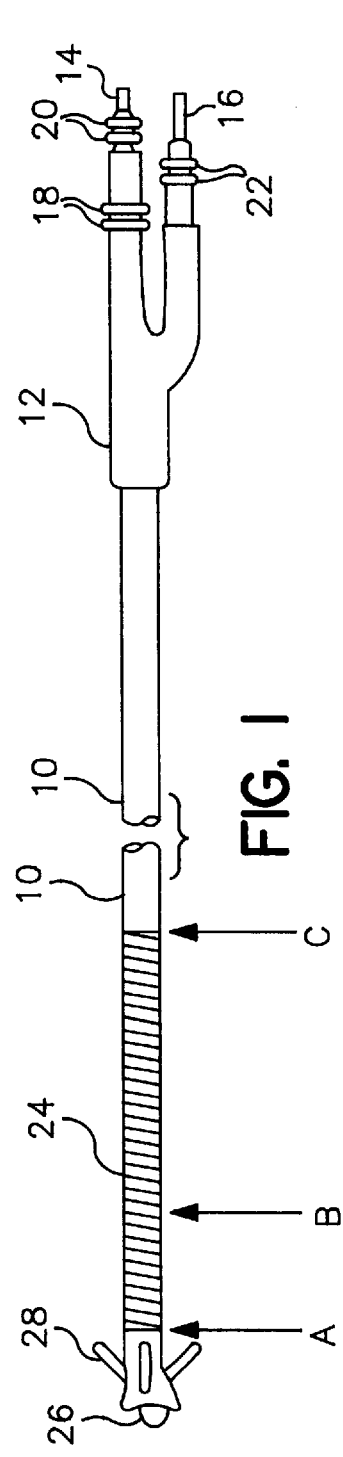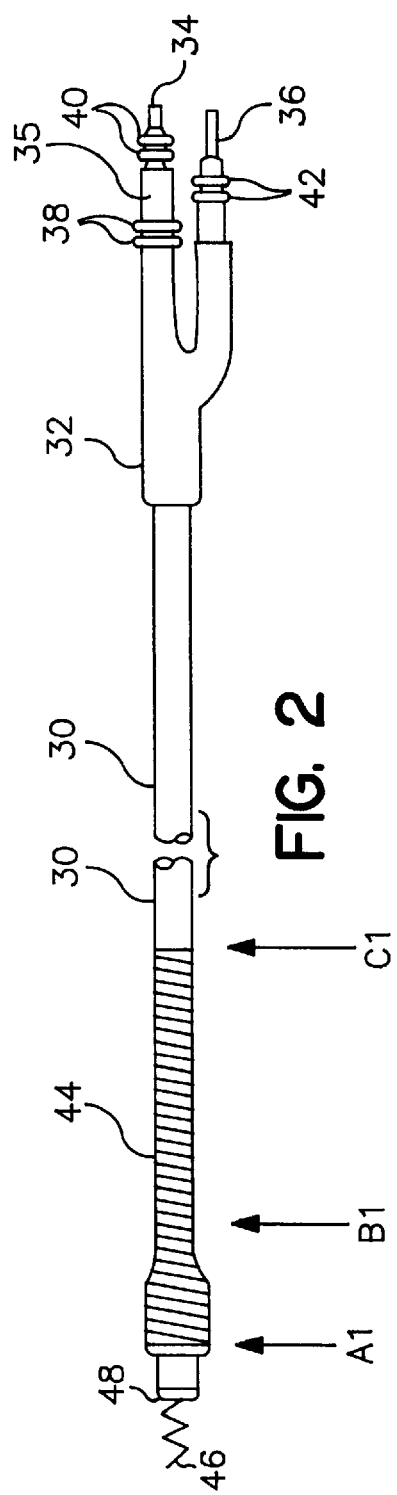

METHOD AND APPARATUS FOR TERMINATION OF TACHYARRHYTHMIAS

BACKGROUND OF THE INVENTION

The present invention relates generally to stimulators for treatment of tachyarrhythmias by means of high voltage shocks, and more particularly to implantable cardioverters and defibrillators and electrode systems for use in conjunction therewith.

Most presently available implantable cardioverters and defibrillators are provided with an electrode system that includes one or more transvenously insertable leads, to be used alone or in conjunction with an additional subcutaneous electrode, which may take the form of a separately implanted patch electrode or may comprise a portion of the housing of the associated implantable defibrillator. Such defibrillator and electrode systems are illustrated in U.S. Pat. No. 4,953,551 issued to Mehra et al. and U.S. Pat. No. 5,014,696 issued to Mehra and U.S. Pat. No. 5,261,400 issued to Bardy. Transvenously implantable electrodes in such systems may include electrodes located in the right ventricle, the coronary sinus/great vein, the superior vena cava/right atrium, or other locations. The subcutaneous electrodes are typically implanted in the left pectoral or left axillary regions of the patient's body.

Most presently available implantable cardioverters and defibrillators employ an asymmetric biphasic waveform, the first phase of the waveform having a leading edge amplitude approximately equal to the voltage to which the high voltage capacitors of the implantable defibrillator are charged, the second phase of the waveform having a leading edge voltage approximately equal to the trailing edge voltage of the first phase of the waveform. Such asymmetric biphasic waveforms are disclosed in U.S. Pat. No. 4,953,551 issued to Mehra et al., U.S. Pat. No. 5,107,834 issued to Ideker et al., U.S. Pat. No. 4,821,723 issued to Baker, Jr. et and U.S. Pat. No. 4,850,357 issued to Bach.

Transvenous defibrillation electrodes typically take the form of an elongated coil, as disclosed in the above-cited references. Typically, current density during delivery of the shock varies along the length of the coil, with the highest current densities found at the ends of the coil, and the lowest current density found toward the middle portion of the coil. Efforts to equalize current distribution along the coil have included altering the location of the connection to the center of the coil as disclosed in U.S. Pat. No. 5,265,623 issued to Kroll et al., and dividing the electrode into individual sub-electrodes, sequentially activated, as in U.S. Pat. No. 4,969,463 issued to Dahl et al. It has also been proposed to provide electrodes having areas of differing conductivity to equalize current distribution during delivery of the pulse as disclosed in U.S. Pat. No. 4,496,362 issued to Kenknight et al. and 5,016,645, issued to Williams et al.

Electrode materials for cardiac defibrillation electrodes include platinum/ iridium, as disclosed in U.S. Pat. No. 4,817,634 issued to Holleman et al, tantalum as disclosed in U.S. Pat. No. 5,224,491 issued to Mehra, metal coated carbon as disclosed in U.S. Pat. No. 5,336,254 issued to Brennen et al., carbon fibers as disclosed in U.S. Pat. No. 5,143,089, issued to Alt, and copper-zirconium alloy coated with tantalum as disclosed in U.S. Pat. No. 4,922,927 issued to Fine, et al. In the context of cardiac pacing and nerve stimulation electrodes, a wider variety of materials has been proposed, including the materials cited above for use in conjunction with defibrillation electrodes, and also including Elgiloy, titanium, zirconium, niobium, molybdenum, hafnium, tantalum or tungsten, as well as oxides, carbides, nitrides and carbonitrides of some or all of the preceding listed metals. Such pacing electrodes are disclosed in U.S. Pat. No. 4,440,178 issued to Bussard, U.S. Pat. No. 5,312,439 issued to Loeb, U.S. Pat. No. 4,602,637 issued to Elmqvist et al, U.S. Pat. No. 4,603,704 issued to Mund et al, U.S. Pat. No. 4,679,572 issued to Baker, U.S. Pat. No. 5,326,448 issued to Otten and U.S. Pat. No. 5,193,540 issued to Schulman et al. The use of tantalum carbide, nitride and carbonitride is disclosed in the cited Elmqvist et al '637 patent and the '704 Mund patent. Use of tantalum electrodes anodized to produce tantalum oxide is disclosed in the above cited '439 Loeb patent and the '540 Schulman et al patent. The use of tantalum as a lead conductor is also suggested in U.S. Pat. No. 4,608,986 issued to Beranek et al. In the context of pacing and nerve stimulation electrodes employing oxides, nitrides, carbides or carbonitrides, the electrodes are intended to provide a capacitive interface between the stimulator and the tissue, which is feasible due to the relatively low amplitude and low energy level of delivered cardiac pacing and nerve stimulation pulses.

SUMMARY OF THE INVENTION

The present invention is directed toward cardiac defibrillation and cardioversion systems employing cardioversion/defibrillation electrodes particularly optimized for use in conjunction with a pulse generator providing an asymmetric biphasic waveform. All or portions of the electrodes are constructed to display differential conductivity as a function of polarity of the applied defibrillation pulses. In particular, the electrodes are configured so that all or a portion of the electrode provide an increased attenuation of electrical current of the polarity of the higher amplitude phase of the applied asymmetric biphasic fibrillation pulse waveform as compared to attenuation of the lower amplitude, opposite polarity phase of the biphasic pulse.

In a first set of embodiments of the invention, portions of the electrode are constructed to display the required differential attenuation in areas in which diminution of the current density during the higher amplitude phase of the biphasic pulse is desired. For example, in the context of an electrode located in the right ventricle, the distal portion of the electrode most closely adjacent to associated cardiac pacing and sensing electrodes may display an increased attenuation of current density during the leading phase of an asymmetric biphasic pulse, effectively shifting the delivered electrical energy during the higher amplitude phase of the pulse somewhat proximally, minimizing the potential for tissue damage adjacent the cardiac pacing and sensing electrodes, while allowing the entire length of the electrode to deliver energy essentially undiminished along the length of the electrode during the lower amplitude phase of the pulse. The diminution of current density adjacent the pacing and sensing electrodes also reduces the likelihood of stunning the tissue, reduces the likelihood of post-shock signal R-wave or P-wave signal attenuation due to electroporation and decreases the likelihood of arcing and gas formation adjacent the distal end of the defibrillation electrode during delivery of the shock. Over-all energy delivery during the higher amplitude phase of the biphasic pulse is, however, not significantly reduced. This particular embodiment of the invention is believed to allow a more distal placement of the defibrillation electrode on a transvenous ventricular lead than would otherwise be possible without increasing the risk of tissue damage adjacent the pacing and sensing electrode. An additional embodiment may provide for construction of electrodes having an increased attenuation of the first phase of the biphasic pulse in regions most closely adjacent to other electrodes within the heart, preventing undesirable current shunting directly between the electrodes during the first, higher amplitude of the biphasic pulse.

A second set of embodiments of the present invention may employ three or more electrodes, one or more of which is treated in part or in whole to provide a greater attenuation of the higher amplitude phase of the biphasic pulse in order to effectively shift current distribution between the two phases of the pulse to provide for increased overall current distribution in a manner analogous to that provided by switching circuitry in U.S. Pat. No. 5,324,309 issued to Kallok et al and U.S. Pat. No. 5,306,291 issued to Kroll, both incorporated herein by reference in their entireties. By configuring some or all of the electrodes to display a greater attenuation of the first phase of the biphasic pulse, the overall current distribution in the heart defining the general defibrillation pulse vector may be shifted between first and second phases of the defibrillation pulse without the requirement of additional switching circuitry.

In a preferred embodiment of the invention, all or a portion of the electrode is fabricated of a valve metal, such as tantalum wire, anodized and annealed to provide a durable oxide coating, which in turn provides for the required increased attenuation of the current delivered through the anodized portion of the electrode during one phase of the biphasic pulse. In a first embodiment, the wire is fabricated of platinum-iridium coated tantalum wire, having a portion of the platinum coating removed, and the exposed tantalum portion anodized and annealed. In a second embodiment of the invention, the electrode may be formed of a tantalum wire, having platinum-iridium sputtered over only a portion of its length, with the exposed tantalum portion anodized and annealed. In a third embodiment, the electrode may simply take the form of a tantalum wire, anodized and annealed along its entire length.

In conjunction with the anodizing and annealing of the tantalum wire, it should be noted that the maximum voltage applied during the anodization process may be substantially less than the maximum leading edge amplitude available from the associated implanted cardioverter or defibrillator to which the lead is attached, which amplitude may typically be 600–750 volts. It should also be noted that the capacitance provided by the tantalum oxide coating is substantially less than that which would be required to provide an essentially capacitive coupling for the first phase of the defibrillation electrode. As such, rather than acting as a capacitive coupling during the leading phase of the biphasic pulse, the electrode continues to conduct during delivery of the first phase of the biphasic pulse, but with current density shifted somewhat away from the anodized tantalum portion of the electrode. Particularly in the context of electrodes having one or both ends taking the form of anodized tantalum, the remainder taking the form of platinum-iridium or other similar biocompatible metal, the overall resistance of the electrode during delivery of the first phase of the biphasic pulse is not significantly affected.

BRIEF DESCRIPTION OF THE DRAWINGS

FIG. 1 is a plan view of an implantable cardioversion/defibrillation lead according to the present invention.

FIG. 2 is a plan view of an alternative embodiment of a cardioversion/defibrillation lead according to the present invention.

DETAILED DESCRIPTION OF THE DRAWINGS

Figure 3:
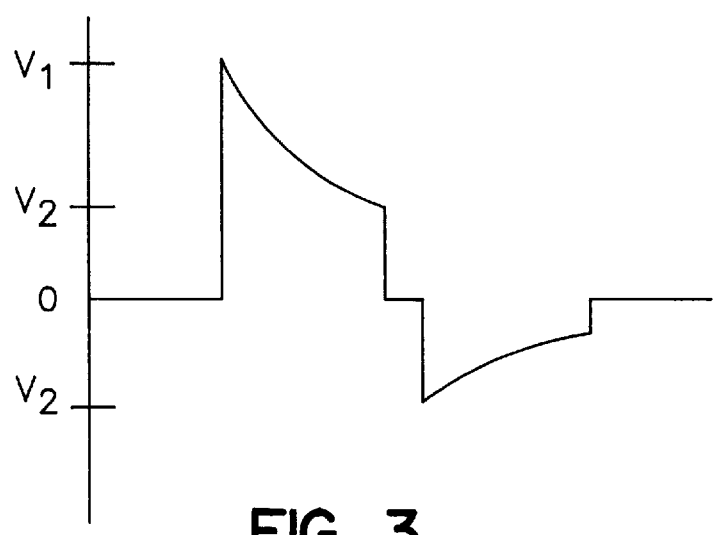
FIG. 3 is a diagram illustrating a biphasic, asymmetric waveform of a type to be delivered using the electrodes illustrated in FIGS. 1 and 2.

FIG. 1 shows a side plan view of a defibrillation lead incorporating the present invention. The lead is provided with an elongated insulative lead body 10 which may be fabricated of polyurethane, silicone rubber or other biocompatible insulative material. Located at the proximal end of the lead is a connector assembly 12 which carries connector pins 14 and 16. Sealing rings 18, 20 and 22 are provided to seal the connector assembly 12 within the connector block of an associated defibrillator. The proximal portion of the lead carries an elongated defibrillation electrode 24 which is fabricated according to the present invention. Electrode 24 includes a first portion extending from point A to point B, which displays an increased attenuation of electrical current of a first polarity, preferably corresponding to the polarity of the higher amplitude phase of a biphasic defibrillation pulse to be applied via the electrode 24 and a second section extending from point B to point C which displays essentially constant attenuation of current density, regardless of polarity of the applied electrical current. The distal end of the lead carries a pacing electrode 26, which may take the form of any of the various commercially available pacing electrodes, and is provided with tines 28 for securing the electrode in place, within the heart. The lead of FIG. 1 is typically employed in the right ventricle of the heart.

The electrode 24 may, for example, take the form of a tantalum wire, coated with platinum-iridium over the length of the coil extending from point B to point C, and not provided with or stripped of the platinum-iridium coating between point A and point B. The exposed tantalum wire between point A and point B is anodized and annealed to provide a coating of tantalum oxide, according to the methods described below.

During delivery of the defibrillation pulse, the portion of the electrode extending from point A to point B displays an increased attenuation of current density during the higher amplitude phase of the pulse, tending to shift current during the highest amplitude portion of the biphasic pulse away from the tissue adjacent to pacing/sensing electrode 26, reducing the likelihood that the tissue will be damaged by delivery of the defibrillation se. Damage to the tissue adjacent to pacing/sensing electrode 26 has the potential of interfering with its ability to accurately sense cardiac depolarizations and of interfering with its ability to reliably pace the heart. Because the current density along the section of the electrode between points A and B is reduced during the highest amplitude portion of the biphasic pulse, the distal end of the defibrillation electrode 24 located at point A may be moved more distally, allowing for over-all improved current distribution near the ventricular apex without increasing the potential for damage to tissue adjacent to pacing/sensing electrode 26.

FIG. 2 is an alternative embodiment of a lead employing the present invention. In particular, the lead of FIG. 2 takes the form of the lead described in U.S. Pat. No. 5,342,414 issued to Mehra, with the substitution of a cardioversion/defibrillation electrode fabricated according to the present invention. The lead is provided with an elongated insulative lead body 30 which carries a connector assembly 32 at its proximal end. Connector assembly 32 carries connector pins 34 and 36 and connector ring 35. Sealing rings 38, 40 and 42 are provided to seal the connector assembly 32 within the connector block of an associated implantable cardioverter defibrillator and to seal between connector ring 35 and connector pin 34. The distal portion of the lead body carries an elongated defibrillation electrode 44 fabricated according to the present invention, displaying increased attenuation of electrical current of the polarity of the first phase of the biphasic pulse between points A1 and B1, and having essentially identical attenuation of current density during both phases of the biphasic pulse along the length of the electrode between points B1 and C1, as described above in conjunction with FIG. 1. The distal portion of the lead carries pace/sense electrodes 46 and 48, electrode 46 taking the form of an advancable helical electrode 46 having only the distal portion thereof uninsulated as described in the above cited Mehra patent, and electrode 48 taking the form of a ring electrode. Ring electrode 48 is coupled to connector ring 35, helical electrode 46 is coupled to pin 34 and defibrillation electrode 44 is coupled to pin 36 by means of mutually insulated conductors extending longitudinally within lead body 30.

FIG. 3 illustrates an asymmetric biphasic waveform of the sort appropriate for use in conjunction with the present invention. As illustrated, the leading edge voltage V1 of the first phase of the pulse is allowed to decay to a trailing edge voltage V2, prior to switching polarity of the pulses. The leading edge voltage negative V2 of the second phase of the pulse is approximately equal in amplitude, but opposite in polarity to the trailing edge voltage V2 of the first pulse. It should be understood that the convention for illustrating the biphasic waveform of FIG. 3, corresponding to that commonly used in the industry, is intended to reflect that the connection between the electrodes across which the voltage is measured has been reversed between the first and second phases of the pulse, rather than suggesting that the first and second phases of the pulse are positive and negative, respectively with regard to a defined ground.

Figure 4:
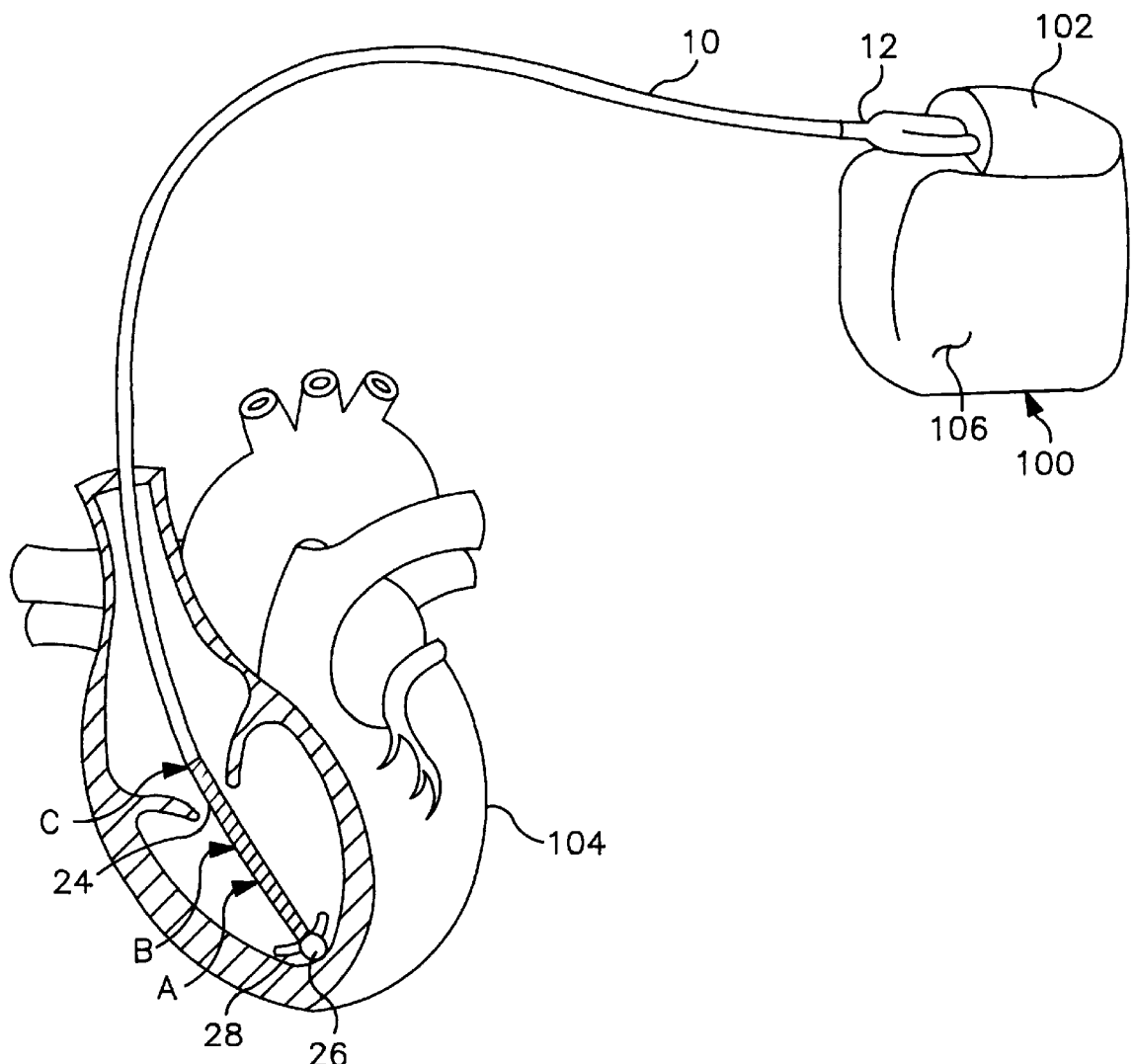
FIG. 4 is a diagram illustrating an implantable cardioverter/defibrillator in conjunction with the lead of FIG. 1, located within a human heart.

FIG. 4 illustrates the electrode of FIG. 1 in conjunction with an implantable cardioverter/defibrillator 100. Connector assembly 12 is inserted in connector block 102 of the cardioverter/defibrillator 100, and the distal portion of the lead is inserted in the right ventricle of the human heart 104, with pace sense electrode 26 located at the right ventricular apex.

It should be understood that within cardioverter/defibrillator 100 are located one or more high voltage capacitors defining a capacitor bank having a first pole coupled to a circuit ground and a second pole adapted to be coupled to a high voltage charging circuit, such that on completion of charging, the capacitor bank retains a voltage of up to plus 750 to plus 800 volts, relative to circuit ground. During the first phase of the delivered biphasic defibrillation pulse, as described in the above Mehra '551 patent, the second pole of the capacitor bank is coupled to electrode 24, and the first pole of the capacitor bank coupled to circuit ground, is coupled to conductive housing 106 of the cardioverter/defibrillator 100. As such, during the first phase of the pulse, current density is shifted somewhat away from pace/sense electrode 26, to reduce the likelihood of tissue damage in the right ventricular apex.

Figure 5:
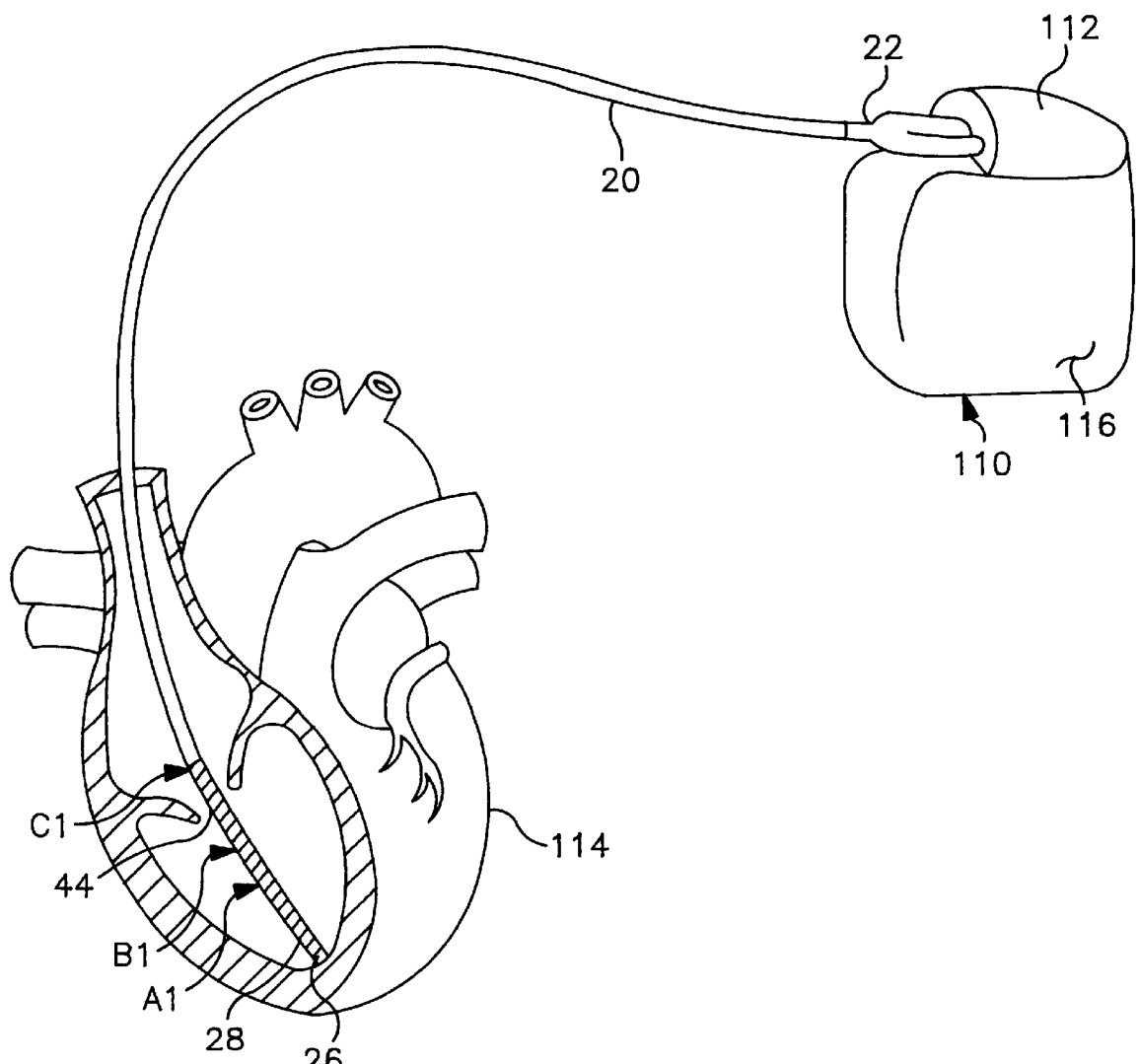
FIG. 5 is a drawing illustrating an implantable cardioverter/defibrillator in conjunction with the lead illustrated in FIG. 2, located inside a human heart.

FIG. 5 illustrates the lead of FIG. 2 in conjunction with an implantable defibrillator 110. Connector assembly 22 is inserted in connector block 112 of the defibrillator and the distal portion of the lead is inserted in the right ventricle of the human heart 114. Helical electrode 26 is illustrated as screwed into the tissue of the heart 114 at the right ventricle apex, with electrode 26 resting adjacent the right ventricular endocardium. As described in conjunction with FIG. 4, during the first phase of the delivered biphasic defibrillation pulse waveform, the portion of cardioversion/defibrillation 44 between points A1 and B1 displays a higher resistance, shifting current density somewhat away from the distal tip of the lead, and reducing the possibility of damage to tissue adjacent pace sensed electrodes 26 and 28 of the first phase of the applied cardioversion/defibrillation pulse.

Figure 6:
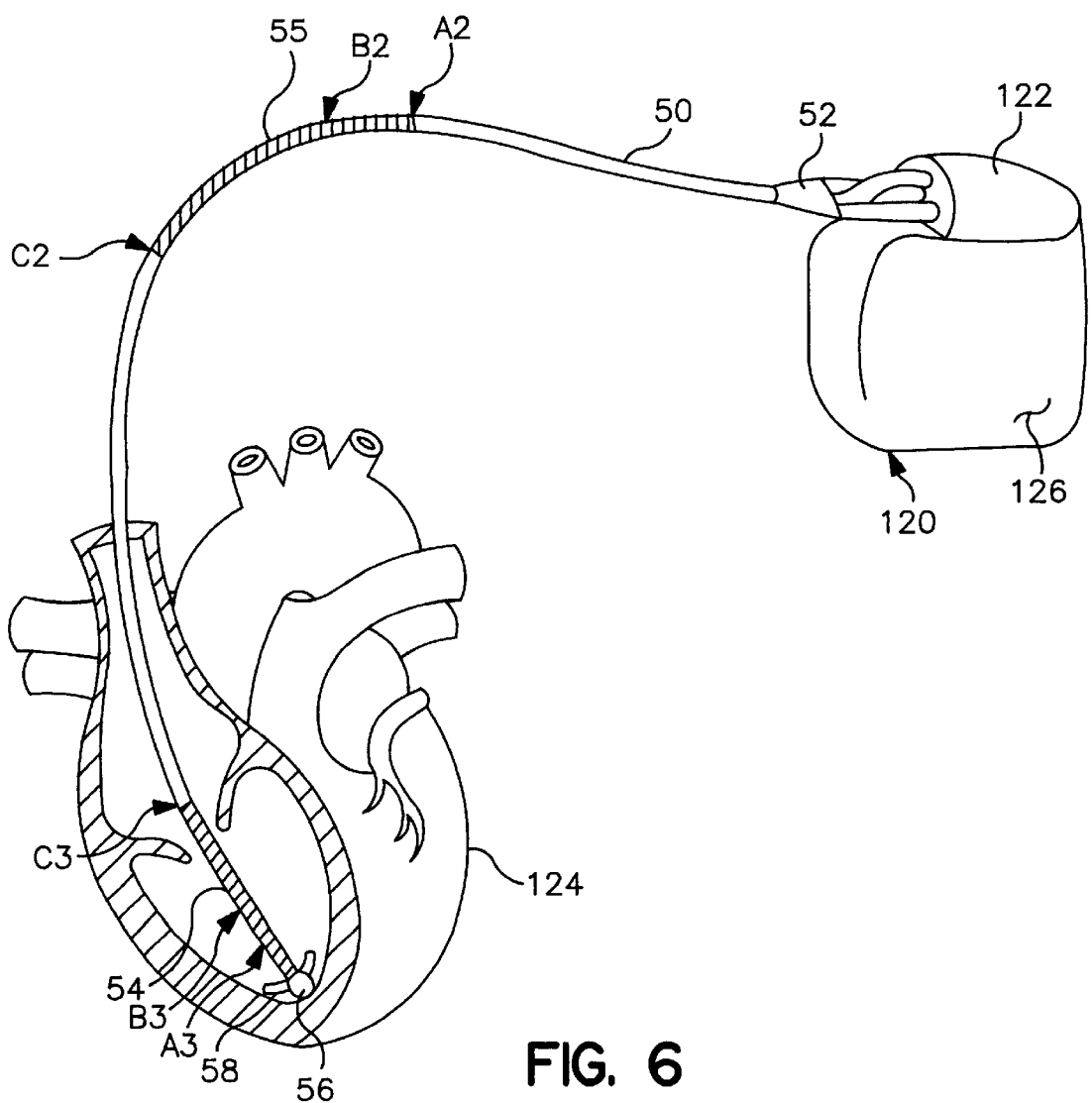
FIG. 6 is an illustration of an implantable cardioverter/defibrillator in conjunction with an alternative lead design employing the present invention, located within the human heart.

FIG. 6 illustrates a third embodiment of the lead according to the present invention in conjunction with an implantable cardioverter defibrillator 120. The lead is provided with an elongated insulative lead body 50 which carries a trifurcated connector assembly 52, which carries three connector pins (not visible), inserted into connector block 122. The lead is also provided with a pace/sense electrode 56, tines 58 and two cardioversion/defibrillation electrodes 54 and 55. Each of the electrodes 54, 55 and 56 is coupled by means of internal conductors to one of the connector pins inserted into the connector block 122 and is thereby coupled to implantable defibrillator 120. The distal portion of the lead is located in the right ventricle of the human heart 124, with pace/sense electrode 56 located at the right ventricular apex. Cardioversion/defibrillation electrode 54 is located in the right ventricle, while defibrillation/cardioversion electrode 55 is located in the superior vena cava, left cephalic vein or left subclavian vein. Portions of electrodes 54 and 55 are constructed to display increased attenuation of current density during the first phase of the biphasic pulse, as discussed above, between points A2 and B2, and A3 and B3, respectively. In this configuration, the overall current vector of defibrillation pulse shifts somewhat between the first and second phases of the pulse. Electrodes 54 and 55 may be coupled in common, and the pulse delivered between these two electrodes and the conductive housing 126 the implantable defibrillator 120, which serves as a third electrode, with electrodes 54 and 55 coupled to the positive voltage stored on the high voltage capacitor bank within defibrillator 120 during the first phase of the biphasic pulse, as described above in conjunction with FIGS. 4 and 5.

Figure 7:
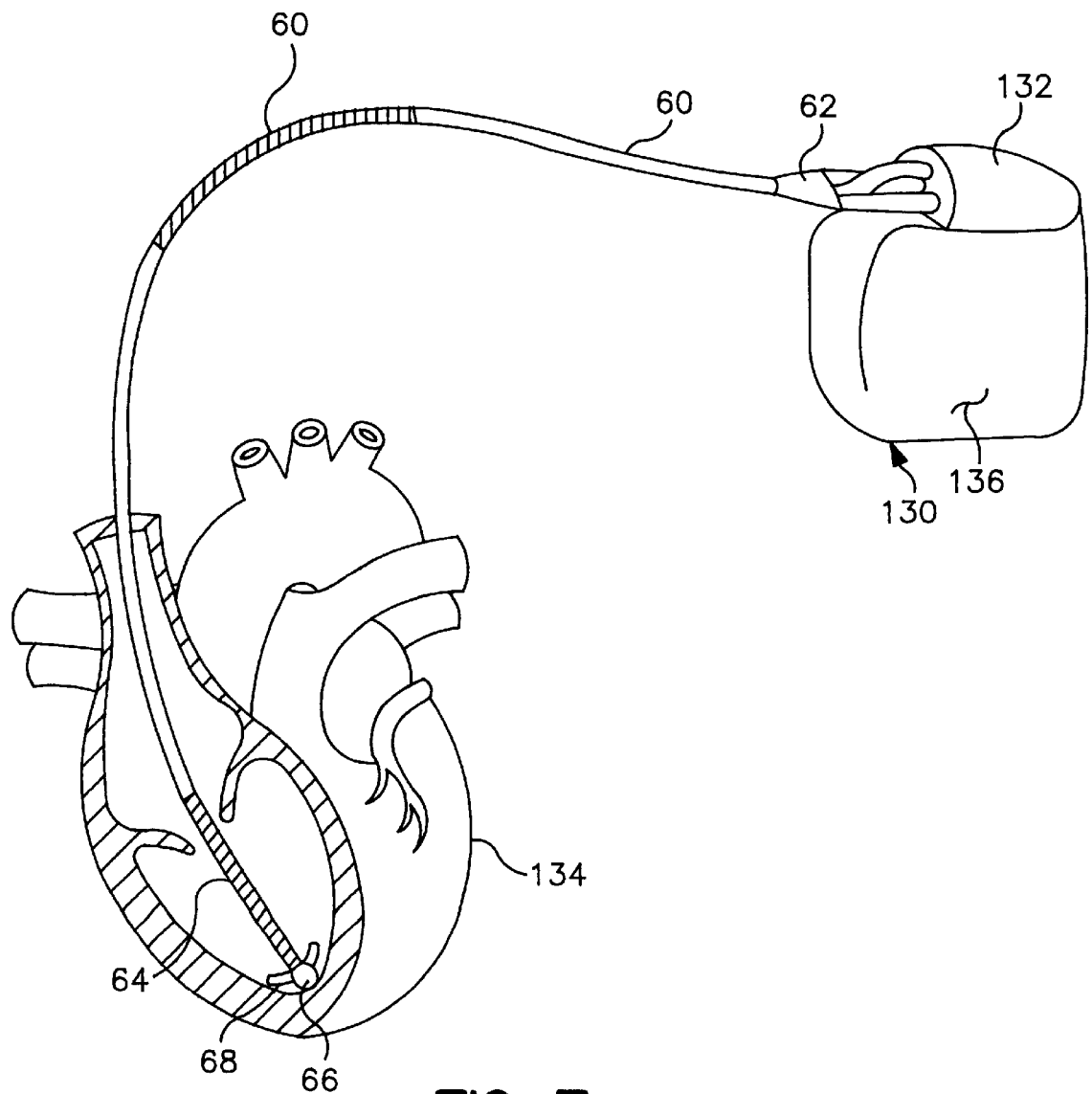
FIG. 7 illustrates an implantable cardioverter in conjunction with a fourth embodiment of an implantable cardioversion/defibrillation lead according to the present invention, located within a human heart.

FIG. 7 illustrates a fourth alternative embodiment of the lead according to the present invention in conjunction with an implantable cardioverter/defibrillator 130. The lead is provided with an elongated lead body 60 which carries a trifurcated connector assembly 62 at its proximal end, in turn carrying three connector pins located within the connector block 132 of defibrillator 130. The lead carries a pace/sense electrode 66 at its distal portion and tines 68, along with two defibrillation electrodes 64 and 65. Electrodes 64, 65 and 66 are each coupled to one of the connector pins on connector assembly 62, and thereby connected to the implantable defibrillator 130. The pace/sense electrode 66 is shown located in the right ventricular apex of the human heart 134, with electrode 64 located in the right ventricle thereof and electrode 65 located in the superior vena cava, left cephalic vein or left subclavian vein.

In this embodiment, electrode 64 takes the form of a platinum-iridium electrode, corresponding to conventional prior art defibrillation electrodes, while electrode 65 takes the form of an electrode in which the entire length of the electrode is configured to display an increased resistance during the higher amplitude phase, typically the first phase, of the applied biphasic pulse. In the context of this embodiment of the invention, electrodes 65 and the conductive housing 136 of the implantable defibrillator 130 may be connected in common to the positive voltage stored on the high voltage capacitor bank within cardioverter/defibrillator 130 during the first phase of the pulse, with electrode 64 coupled to circuit ground, the connections being reversed during the second phase of the delivered pulse. In this context, current is shifted relatively more toward the path defined by electrodes 64 and the housing 136 of the defibrillator during the first phase, and shifted more toward the path defined between electrodes 64 and 65, during the second phase of the pulse.

Figure 8:
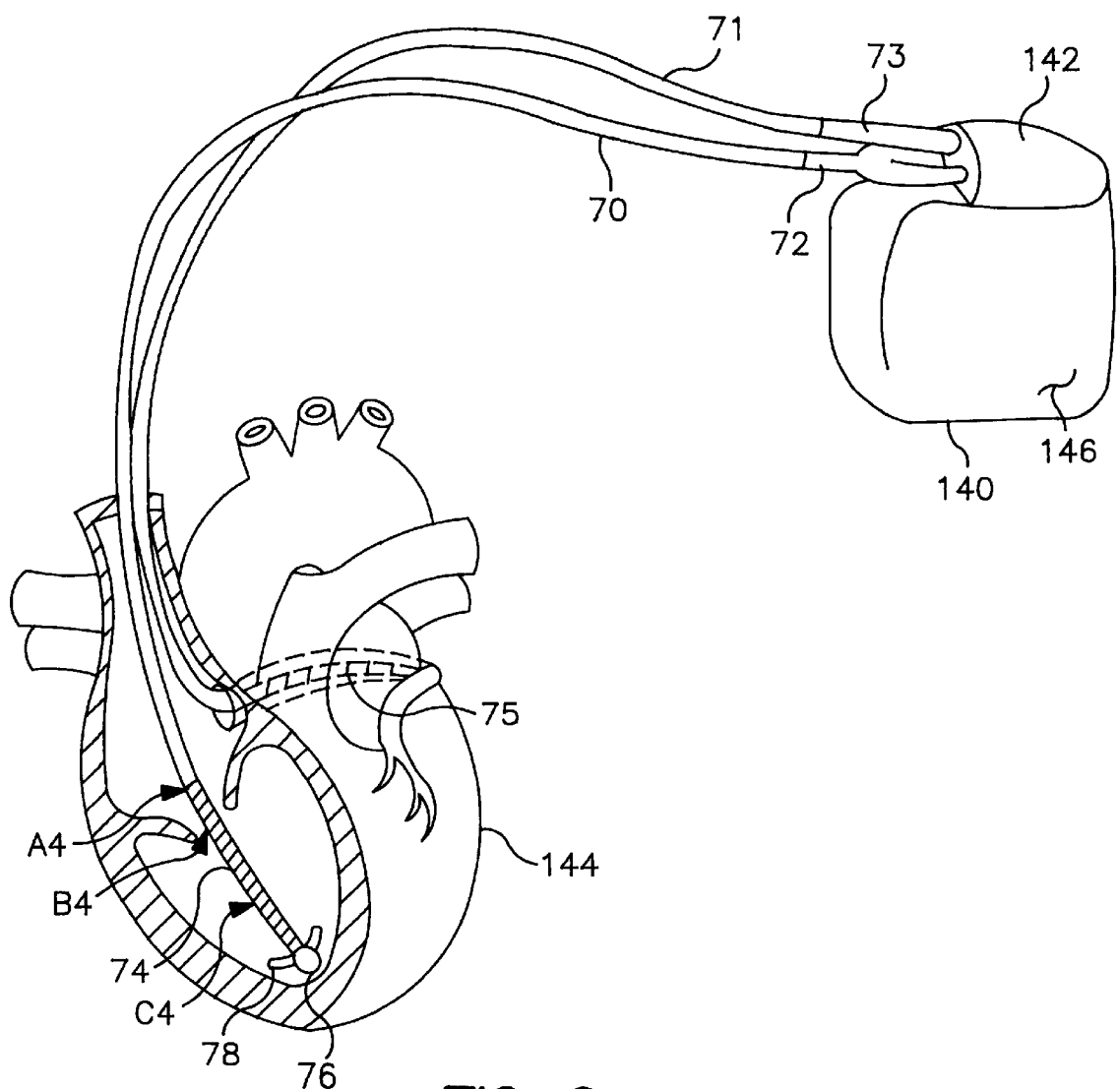
FIG. 8 illustrates an implantable cardioverter/defibrillator in conjunction with a fifth embodiment of an implantable lead system according to the present invention, located within a human heart.

FIG. 8 illustrates a fifth embodiment of a lead system according to the present invention in conjunction with an implantable defibrillator 140. The lead system includes a first lead having elongated lead body 70 and a connector assembly 72 inserted in connector block 142 of defibrillator 140. The first lead is provided with a pace/sense electrode 76 at its distal tip and tines 78, along with a defibrillation electrode 74 fabricated according to the present invention. The second lead is provided with an elongated insulative lead body 71 and a connector assembly 73, also inserted into connector block 142 of defibrillator 140. The second lead is also provided with an elongated defibrillation electrode 75, located in the coronary sinus of the heart 144. Electrode 75 may be a conventional defibrillation electrode, for example, fabricated of a platinum-iridium coil.

Electrode 74 is treated over a portion of its length, extending from point A4 to point B4 to display a higher resistance during the initial phase of the biphasic defibrillation pulse provided by cardioverter/defibrillator 140. During delivery of the biphasic defibrillation shock, electrode 75 is connected in common with the conductive enclosure 146 of defibrillator 140, both of which are coupled to circuit ground. Electrode 74 is coupled to the positive voltage stored on the output capacitor, during the first phase of the biphasic pulse. In the context of the invention as illustrated, the provision of an area of reduced conductivity during the higher amplitude phase of the biphasic pulse assists in moving current density somewhat distally, along electrode 74, preventing shunting between the proximal ends of electrodes 74 and 75.

Figure 9:
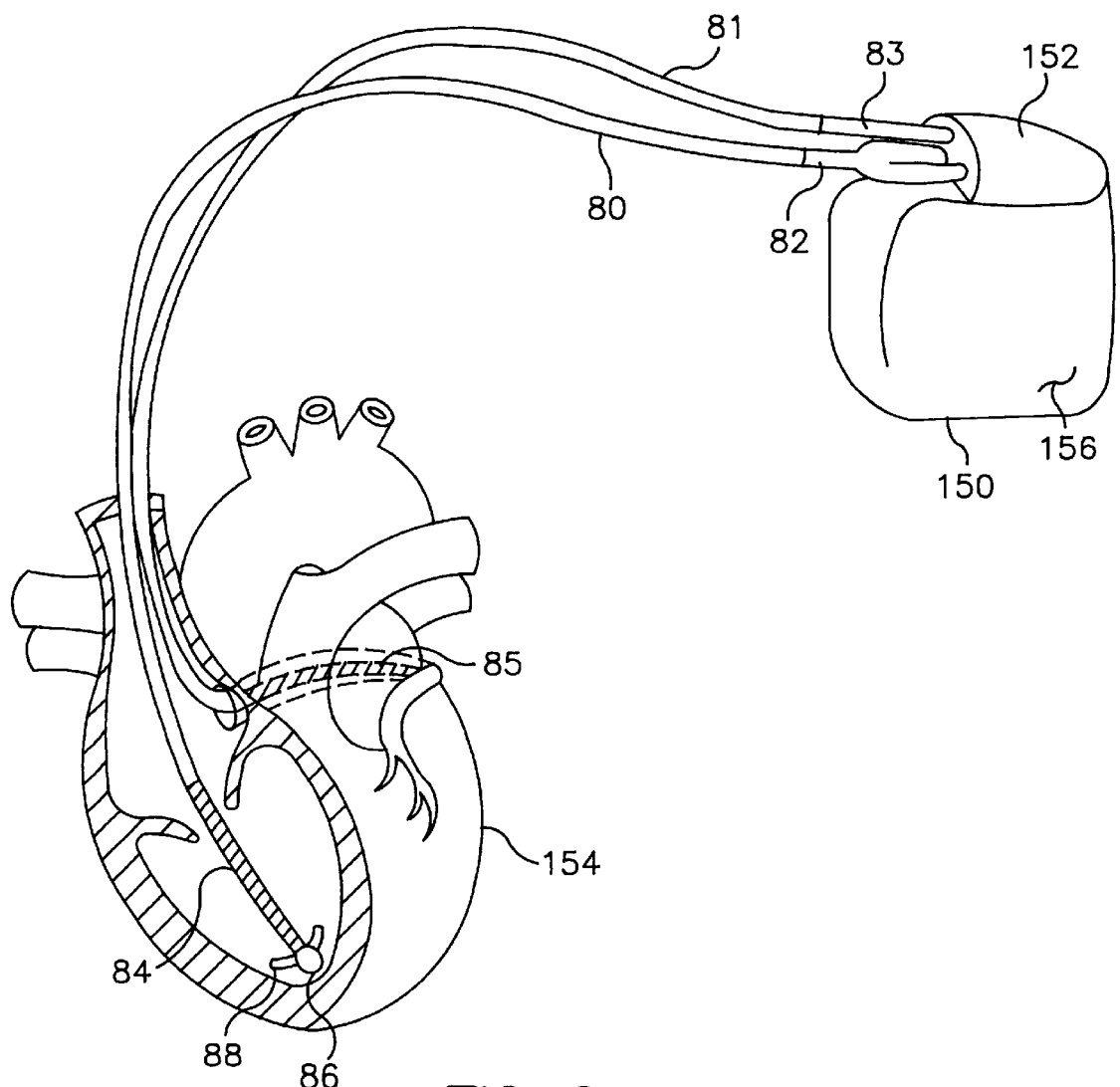
FIG. 9 illustrates an implantable cardioverter/defibrillator in conjunction with a sixth embodiment of a cardioversion/defibrillation lead system according to the present invention, located within a human heart.

FIG. 9 illustrates an implantable cardioverter/defibrillator 150 in conjunction with a seventh alternative lead system embodying the present invention. The lead system illustrated in FIG. 9 includes a first ventricular lead provided with an elongated lead body 80 and carrying a connector assembly 82 inserted in connector block 152 of cardioverter/defibrillator 150. At the proximal end of the ventricular lead are a sense electrode 86, tines 88 and a defibrillation electrode 84, which may correspond to typical prior art defibrillation electrodes fabricated of platinum iridium. The second lead is a coronary sinus lead provided with an elongated insulative lead body 81, a connector assembly 83 inserted in connector block 152 and carrying an elongated defibrillation electrode 85 located in the coronary sinus/great cardiac vein of the human heart 154. Electrode 85 may take the form of a tantalum wire anodized and annealed along its entire length, to provide an attenuation of current flow during the initial phase of the biphasic pulse delivered by implantable cardioverter/defibrillator 150. During the higher amplitude phase of the pulse, electrode 84 may be coupled to circuit ground, with electrode 85 coupled in common with the conductive enclosure 156 of cardioverter/defibrillator 150 and to the positive voltage stored on the output capacitor within cardioverter/defibrillator 150. As such, during the higher amplitude phase of the biphasic pulse, relatively more current is delivered along the axis defined by electrodes 84 and the housing 156 of the defibrillator 150, while during the lower amplitude phase of the pulse, relatively more current is delivered along the axis defined by electrodes 84 and 85.

Figure 10:
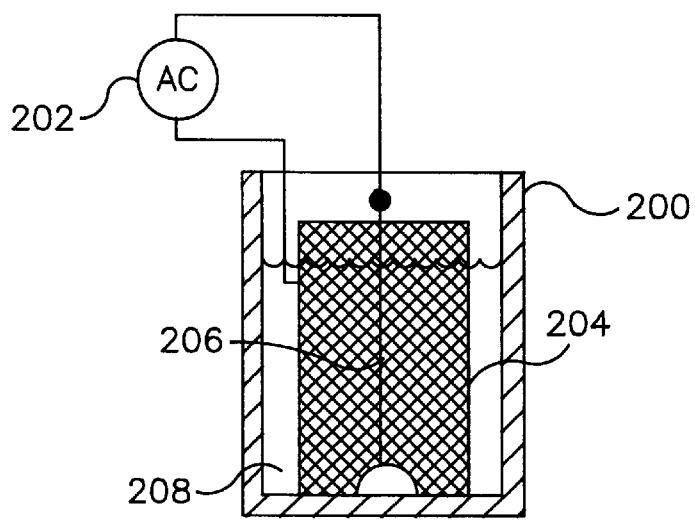
FIG. 10 is a schematic diagram illustrating an electrolytic cell for electrochemical etching or polishing to be employed in conjunction with the manufacture of electrodes according to the present invention.

FIG. 10 is an illustration of an electrolytic cell used in context of the present invention to perform chemical etching and polishing steps associated with producing the electrode patterns according to the present invention. A container 200 is filled with an electrolytic etching solution 208, described in more detail in conjunction with the examples below. A cylindrical screen electrode 240 is provided which surrounds the wire or coil 206 to be etched or polished, to provide for even current distribution along the length of wire 206 and around its circumference. Wire 206 and screen 204 are coupled to a controllable AC electrical source 202. The end of wire 206 is held centered within cylindrical mesh 204 by means of an insulative fixture 210.

Figure 11:
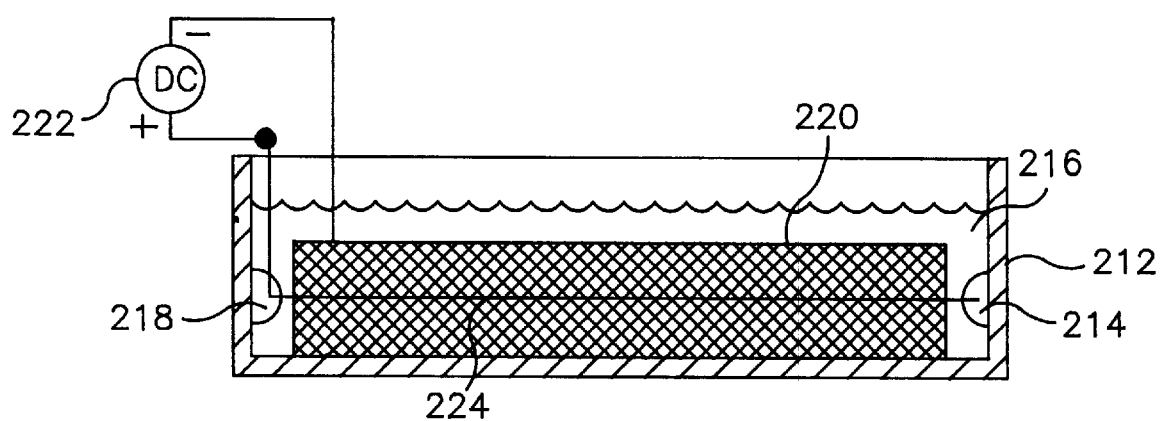
FIG. 11 is a schematic diagram of an electrochemical cell for use in conjunction with anodizing and annealing electrodes according to the present invention.

FIG. 11 illustrates an electrical chemical cell employed in the context of the present invention to perform the anodizing and annealing steps associated with providing the required coating of tantalum oxide over all low portions of electrodes fabricated according to the present invention. A container 212 is filled with an electrolyte solution 216, and contains a cylindrical mesh electrode 220. The wire or coil 224 to be anodized extends through the center of cylindrical mesh electrical 220 and is held in place by insulative fixtures 214 and 218. Mesh 220 and wire 224 are coupled to a controllable DC power source 222. The use of the apparatus illustrated in FIG. 11, as well as the use of the apparatus in FIG. 10 as discussed in more detail below in conjunction with the various examples set forth.

Figure 12:
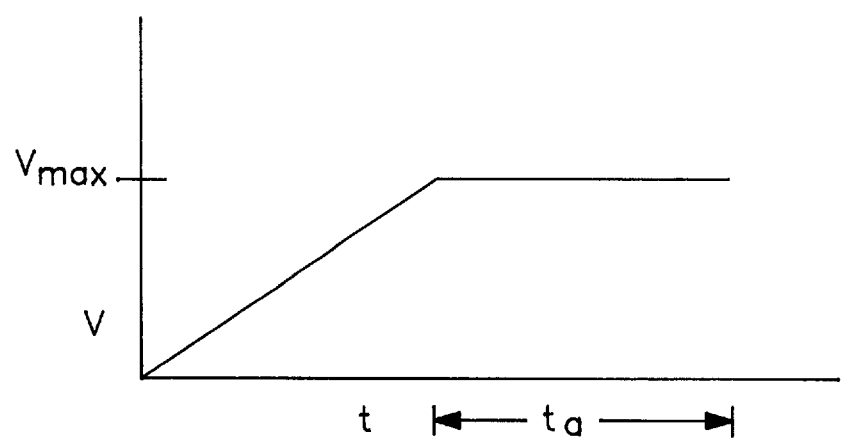
FIG. 12 illustrates a preferred voltage ramp for use in anodizing and annealing electrodes according to the present invention.

FIG. 12 is a voltage versus time graph illustrating the voltage provided by DC power source 222 in FIG. 11, during the electrochemical anodizing and annealing steps associated with fabricating an electrode according to the present invention.

Electrodes according to the present invention may be prepared in accordance with three general types of processes, referred to hereafter as process 1, process 2, and process 3. Process 1 comprises anodizing and annealing a tantalum wire to produce an electrode which exhibits an increased attenuation of current flow during the first phase of the biphasic defibrillation pulse over its entire length. Process 2 produces an electrode according to the present invention by starting with a platinum-iridium clad tantalum wire, etching off a portion or portions of the platinum-iridium to expose a portion or portions of the underlying tantalum wire, and thereafter oxidizing and annealing the exposed tantalum wire. Process 3 comprises covering or plating a portion of a tantalum wire with platinum-iridium by sputtering, chemical vapor deposition, physical vapor deposition, ion implantation or other method, followed by anodizing and annealing the remaining exposed tantalum surface of the wire.

In conjunction with Process 2 and Process 3, other low polarization alloys or metals such as 70Pt/30Ir, TiN, Ru, etc. may be substituted for the 90Pt/10Ir alloy coating or plating employed in the following examples. In conjunction with all three processes, other valve metals, including nano-engineered and semiconducting metals may be substituted for tantalum.

EXAMPLE 1
PROCESS 1

Three to five feet of 0.010 inch diameter tantalum wire are first degreased in Micro(R) detergent cleaning solution at room temperature for 5–10 minutes in an ultrasonicator. The wire is thereafter immersed for one to two seconds in an approximately 2:2:5 mixture by volume of hydrochloric acid, nitric acid, and sulfuric acid, in order to etch off any surface oxidation already present on the tantalum wire. The wire is thereafter rinsed in 18M ohm deionized water, and thereafter boiled in 18M ohm deionized water for 30 minutes. The wire is then dried with clean air or nitrogen, and optionally is electrolytically etched, for example, for one minute, in an electrolytic solution comprising 20 grams of ammonium bromide per liter of ethanol, including 1.5% by weight 18M ohm deionized water, at a voltage sufficient to provide a current level of 0.5 to 2.5 milliamp per square millimeter of wire to be etched. The wire is thereafter anodized, for example, using the apparatus illustrated in FIG. 11, in an electrolytic solution of 0.1–1.0% by volume of $H_2SO_4$ or $H_3PO_4$. The counter-electrode may be a tantalum cylindrical screen, as generally illustrated in FIG. 11, and the DC power supply 222 may be employed to provide a voltage of from 0 to 200 volts, rising at 8 millivolts per second, to anodize the wire, followed by the application of DC current at 200 volts for 10 to 30 minutes thereafter to anneal the oxide surface. The wire is then rinsed twice in 18M ohm deionized water, dried and coiled to provide a coil electrode. The anodizing and annealing steps may be repeated following coiling of the wire, in order to assure that no voids or breaks are present in the tantalum oxide surface.

EXAMPLE 2
PROCESS 2

A portion of a 0.01 inch diameter platinum-iridium clad tantalum wire is etched in hot aqua regia under mild agitation for a period of approximately five hours, to remove the platinum-iridium coating over a portion of the wire. The wire is then degreased, boiled and etched as in example 1 above, and thereafter anodized. The wire may be anodized using the apparatus illustrated in FIG. 11, employing an electrolytic solution of 0.01 Molar aqueous ammonium tartrate, at a current density of 10–30 milliamps per square centimeter of wire to be anodized, rising from 0 to a maximum voltage of 200 volts as illustrated in FIG. 12. The voltage is thereafter maintained for 200 volts for a period of 15–30 minutes in order to anneal the tantalum oxide coating. The wire is then removed from the electrochemical cell, cleaned with deionized water and wound into a coil configuration. The anodizing and annealing steps are repeated thereafter in order to assure that there are no breaches or breaks in the tantalum oxide coating.

EXAMPLE 3
PROCESS 2

A platinum-iridium clad tantalum wire as described in Example 2 is electrolytically etched, for example, using the apparatus illustrated in FIG. 10 to remove the platinum iridium coating over a portion of the wire, exposing the tantalum wire underneath. Electrolytic etching may take place in a etching solution comprising 36% by volume 18M ohm deionized water, 60% by volume calcium chloride and 4% by volume hydrochloric acid. Etching may take place at a voltage of 6 volts AC, at a frequency of 10 to 500 Hz, at 25–45 degrees centigrade. The wire is thereafter polished and etched according to Example 1, thereafter anodized using the apparatus of FIG. 11, employing the anodization and annealing steps set forth in conjunction with Example 1 or Example 2 above. The electrolytic etching step employed to remove the platinum iridium cladding from the wire in this example is believed preferable to that employed in conjunction with example 3, given the substantially reduced toxicity of the etching solution, and the substantially more rapid removal of the platinum iridium cladding.

EXAMPLE 4
PROCESS 2

A length of 0.01 inch diameter platinum-iridium clad wire is first degreased in Micro(R) cleaning solution for 10 minutes in an ultrasonicator as described in conjunction with example 1, and then electrolytically etched using the apparatus of FIG. 10 in order to remove the platinum iridium cladding over a portion of the wire, by inserting that portion of the wire into an etching fluid comprising 25% by volume potassium cyanate (KCN) in water, and electrolytically etched at 10 to 500 Hz AC at a voltage sufficient to maintain a current density of 50–400 square centimeter of wire to be etched. The wire is then removed from the electrolytic cell and polished if necessary as per example 1, and thereafter anodized and re-anodized as per example 3 above.

EXAMPLE 5
PROCESS 3

An 010 inch tantalum wire is sputter coated over a portion of its length using the sputter coating apparatus set forth in U.S. Pat. No. 4,860,446 issued to Lessar et al. incorporated herein by reference in its entirety to produce a 5,000 to 8,000 angstrom coating of platinum-iridium over the tantalum wire. The wire is then degreased and chemically polished according to the method of example 1 above, and thereafter anodized, annealed, coiled re-anodized and re-annealed according to the method of example 2 set forth above.

EXAMPLE 6
PROCESS 3

An 010 inch tantalum wire is sputter coated over its entire length using the apparatus of U.S. Pat. No. 4,860,446 issued to Lessar et al. cited above. A portion of the wire is then electrolytically etched according to the method of example 2, to remove platinum-iridium over a portion or portions of the length of the wire, and is thereafter chemically polished and boiled according to the method of example 1, and anodized, annealed, coiled, re-anoidized and re-annealed according to the method set forth in example 2.

In conjunction with Process 2 and Process 3, it should also be noted that more complicated patterns of platinum/iridium and annealed tantalum may be produced by employing photo-resist or other photolithographic processes to define multiple regions on which the Pt/Ir coating is etched away. Electrodes having multiple, spaced regions of exposed annealed tantalum may thus be produced and are also within the scope of the present invention. In conjunction with Process 3, termination of the etching step can occur in connection with a drop in measured current through the etching cell which occurs on disappearance of the Pt/Ir coating on that portion of the wire immersed in the electrolyte solution.

The above methods employed for producing electrodes comprising a length of tantalum wire, oxidized and annealed according to the procedures set forth, result in an electrode with a durable coating of tantalum oxide, substantially thicker and more consistent than would result from the oxidation which naturally occurs to tantalum wire in the atmosphere, or the oxidation there which occurs naturally as a result of applied electrical current during delivery of defibrillation or cardioversion pulses, if such wire is employed as an electrode. The resultant structure provides an electrode which displays over either all or part of its length a substantially increased attenuation of current density during positive electrical current pulses, as desired in the context of the present invention.

While all of the above examples employ electrodes having only one portion of the electrode treated to display increased attenuation of current density during the positive phase of the biphasic defibrillation pulse, it should be noted that electrodes in which multiple zones of increased attenuation of positive current pulses are also within the scope of the present invention. For example, in the context of a lead otherwise as illustrated in FIG. 1, two areas of increased attenuation of positive current pulses may be provided, one at the proximal end of the electrode and one at the distal end of the distal end of the electrode, if desired. It should also be noted that in spite of the fact that all of the examples herein specifically employ tantalum as the base wire for the electrode and platinum iridium as a coating, where needed, other embodiments are also workable. For example, wires fabricated of a metal which displays essentially equal attenuation of positive and negative current pulses may be coated with an outer coating of tantalum, which is thereafter anodized and annealed to provide increased attenuation of to positive pulses may be substituted. Similarly, as discussed above, other metals or combinations of metals having similar characteristics may also be employed in the context of the present invention.

It should also be noted that while the examples set forth herein deal specifically with anodization and annealing of electrodes for location on implantable transvenous leads, the same process may be applied to epicardial or subcutaneous electrodes or to the pulse generator housing or a portion of the pulse generator housing, which as discussed above, may also serve as an electrode. As such, the examples set forth herein should be considered exemplary, rather than limiting with regard to the claims which follow.

In conjunction with the above specification,
We claim:

1. A implantable medical lead, comprising:
    an elongated insulative lead body carrying a cardioversion/defibrillation electrode, wherein the cardioversion/defibrillation electrode comprises a first portion displaying essentially equal attenuation of positive and negative voltage pulses and a second portion displaying differential attenuation of positive and negative voltage pulses.

2. A lead according to claim 1 wherein the lead body further carries a cardiac pacing electrode and wherein the second portion of the cardioversion/defibrillation electrode is located more closely to the pacing electrode than is the first portion of the cardioversion/defibrillation electrode.

3. A lead according to claim 1 wherein the lead body further carries a cardiac sensing electrode and wherein the second portion of the cardioversion/defibrillation electrode is located more closely to the sense electrode than is the first portion of the cardioversion/defibrillation electrode.

4. A lead according to claim 1 or claim 2 or claim 3 wherein the cardioversion electrode is an elongated coil electrode.

5. A lead according to claim 1 or claim 2 or claim 3 wherein the second portion of the cardioversion/defibrillation electrode displays an increased attenuation of positive voltage pulses.

6. An implantable cardioversion/defibrillation system, comprising:
    an implantable cardioverter/defibrillator comprising means for generating biphasic output pulses;
    a plurality of cardioversion/defibrillation electrodes, coupled to said pulse generating means, said electrodes comprising a first electrode portion displaying essentially equal attenuation of positive and negative voltage pulses and a second electrode portion displaying differential attenuation of positive and negative voltage pulses.

7. A system according to claim 6 wherein the first electrode portion is a portion of a first one of the cardioversion/defibrillation electrodes and the second electrode portion is a portion of a second one of the cardioversion/defibrillation electrodes.

8. A system according to claim 7 wherein the second electrode portion comprises all of the second one of the cardioversion/defibrillation electrodes.

9. A system according to claim 8 wherein the first electrode portion comprises all of the first one of the cardioversion/defibrillation electrodes.

10. A system according to claim 6 wherein the first and second electrode portions are both portions of a first one of the cardioversion/defibrillation electrodes.

11. A system according to claim 6 or claim 7 or claim 8 or claim 9 or claim 10 wherein the cardioversion/defibrillation electrodes are elongated coil electrodes.

12. A system according to claim 6 or claim 7 or claim 8 or claim 9 or claim 10 wherein the second electrode portion displays an increased attenuation of positive voltage pulses.

13. A system according to claim 6 or claim 7 or claim 8 or claim 9 or claim 10 wherein the pulse generating means comprises means for generating asymmetric biphasic pulses in which a first phase of the pulse has greater amplitude than a second phase and wherein the second electrode portion displays an increased attenuation of the first phase of the pulse.

14. A implantable medical lead, comprising:
    an elongated insulative lead body carrying a cardioversion/defibrillation electrode, wherein the cardioversion/defibrillation electrode comprises a first portion displaying essentially equal attenuation of positive and negative voltage pulses and a second portion having an exterior surface of tantalum oxide.

15. A lead according to claim 14 wherein the lead body further carries a cardiac pacing electrode and wherein the second portion of the cardioversion/defibrillation electrode is located more closely to the pacing electrode than is the first portion of the cardioversion/defibrillation electrode.

16. A lead according to claim 14 wherein the lead body further carries a cardiac sensing electrode and wherein the second portion of the cardioversion/defibrillation electrode is located more closely to the sense electrode than is the first portion of the cardioversion/defibrillation electrode.

17. A lead according to claim 15 or claim 15 or claim 16 wherein the cardioversion electrode is an elongated coil electrode.

18. An implantable cardioversion/defibrillation system, comprising:

an implantable cardioverter/defibrillator comprising means for generating biphasic output pulses;

a plurality of cardioversion/defibrillation electrodes, coupled to said pulse generating means, said electrodes comprising a first electrode portion displaying essentially equal attenuation of positive and negative voltage pulses and a second electrode portion having an exterior surface of tantalum oxide.

19. A system according to claim 18 wherein the first electrode portion is a portion of a first one of the cardioversion/defibrillation electrodes and the second electrode portion is a portion of a second one of the cardioversion/defibrillation electrodes.

20. A system according to claim 18 wherein the second electrode portion comprises all of the second one of the cardioversion/defibrillation electrodes.

21. A system according to claim 20 wherein the first electrode portion comprises all of the first one of the cardioversion/defibrillation electrodes.

22. A system according to claim 18 wherein the first and second electrode portions are both portions of a first one of the cardioversion/defibrillation electrodes.

23. A system according to claim 18 or claim 19 or claim 20 or claim 21 or claim 22 wherein the cardioversion/defibrillation electrodes are elongated coil electrodes.

24. A system according to claim 18 or claim 19 or claim 20 or claim 21 or claim 22 wherein the pulse generating means comprises means for generating asymmetric biphasic pulses in which a first, positive voltage phase of the pulse has greater amplitude than a second, negative voltage phase.

25. A method of fabricating a cardioversion/defibrillation lead, comprising:

selecting a metal member fabricated of a first material capable of displaying unequal attenuation of positive and negative voltage pulses, coated with a second material displaying essentially equal attenuation of positive and negative voltage pulses;

removing a portion of said second material to expose a portion of said first material;

mounting said member to an insulative lead body and coupling said member to a conductor located within said lead body.

26. A method according to claim 25 wherein said selecting step comprises selecting a member fabricated of a first material which is tantalum.

27. A method according to claim 25 or 26 comprising the step of treating said exposed portion of said first material to cause said exposed portion of said first material to display said differential attenuation.

28. A method according to claim 27 wherein said treating step comprises anodizing said exposed portion of said first material.

29. A method of fabricating a cardioversion/defibrillation lead, comprising:

selecting a metal member fabricated of a first material capable of displaying unequal attenuation of positive and negative voltage pulses;

coating a portion of said first material with a second material displaying essentially equal attenuation of positive and negative voltage pulses;

mounting said member to an insulative lead body and coupling said member to a conductor located within said lead body.

30. A method according to claim 29 wherein said selecting step comprises selecting a member fabricated of a first material which is tantalum.

31. A method according to claim 29 or 30 comprising the step of treating said exposed portion of said first material to cause said exposed portion of said first material to display said differential attenuation.

32. A method according to claim 31 wherein said treating step comprises anodizing said exposed portion of said first material.

33. A method of fabricating a cardioversion/defibrillation lead for delivery of defibrillation pulses having a first expected voltage, comprising:

selecting a metal member fabricated of displaying a first material capable of displaying unequal attenuation of positive and negative voltage pulses when anodized;

anodizing said member at a voltage less than said first expected voltage; and thereafter mounting said member to an insulative lead body and coupling said member to a conductor located within said lead body.

34. A method according to claim 33 wherein said selecting step comprises selecting a member fabricated of a first material which is tantalum.

35. A method according to claim 33 or claim 34, further comprising the step of providing a coating of a second material displaying essentially equal attenuation of positive and negative voltage pulses over a portion of said member, prior to said anodizing step.

36. A method according to claim 33 or claim 34 wherein said selecting step comprises selecting a member fabricated of a first material capable of displaying unequal attenuation of positive and negative voltage pulses when anodized, coated with a second material displaying essentially equal attenuation of positive and negative voltage pulses; further comprising the step of removing a portion of said second material to expose a portion of said first material prior to said anodizing step.

* * * * *